US010588722B2

(12) United States Patent
Demarest et al.

(10) Patent No.: US 10,588,722 B2
(45) Date of Patent: Mar. 17, 2020

(54) MULTI-CHEMISTRY DISPENSER

(71) Applicant: Colgate-Palmolive Company, New York, NY (US)

(72) Inventors: Scott Demarest, Basking Ridge, NJ (US); Jo Fleming, San Diego, CA (US); David Neese, San Diego, CA (US); Michael Gordon, San Diego, CA (US); David Berardelli, San Diego, CA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/753,243

(22) PCT Filed: Aug. 19, 2015

(86) PCT No.: PCT/US2015/045829
§ 371 (c)(1),
(2) Date: Feb. 16, 2018

(87) PCT Pub. No.: WO2017/030576
PCT Pub. Date: Feb. 23, 2017

(65) Prior Publication Data
US 2019/0015180 A1 Jan. 17, 2019

(51) Int. Cl.
*A61C 9/00* (2006.01)
*A61C 5/64* (2017.01)
(Continued)

(52) U.S. Cl.
CPC .............. *A61C 9/0026* (2013.01); *A61C 5/62* (2017.02); *A61C 5/64* (2017.02); *A61C 19/066* (2013.01); *B05C 17/00553* (2013.01)

(58) Field of Classification Search
CPC ..... B05C 17/00553; A61C 9/026; A61C 5/62; A61C 5/64; A61C 5/68; A61C 19/066; A61C 9/0026
(Continued)

(56) References Cited

U.S. PATENT DOCUMENTS 3,363,811 A  1/1968 Geist, Sr.
5,722,829 A  3/1998 Wilcox et al.
(Continued)

FOREIGN PATENT DOCUMENTS

| CA | 2721477 | 12/2009 |
| WO | 2005/016783 | 2/2005 |
| WO | 2011/137437 | 11/2011 |

OTHER PUBLICATIONS

KM Mixers, http://www.chemineer.com/products/kenics/km-mixers.html, accessed May 19, 2015, 1 page.
(Continued)

*Primary Examiner* — Paul R Durand
*Assistant Examiner* — Andrew P Bainbridge

(57) ABSTRACT

A dispenser for dispensing a liquid such as a tooth whitening gel can include a plunger and a housing having a first chamber that receives a first arm of the plunger and a second chamber that receives a second arm of the plunger. The housing can further include a first channel in fluid communication with the first chamber, a second channel in fluid communication with the second chamber, and a third channel formed at an intersection of the first and second channels. The housing can further include a static mixer than mixes a first liquid from the first chamber with a second liquid from the second chamber. The plunger may be disposed along a first axis and the third channel may be disposed along a second axis that intersects the first axis at an angle of between 10° and 170°.

18 Claims, 2 Drawing Sheets

(51) Int. Cl.
*A61C 19/06* (2006.01)
*A61C 5/62* (2017.01)
*B05C 17/005* (2006.01)

(58) Field of Classification Search
USPC .......................... 222/134–137, 145.5–145.6,
222/153.05–153.06, 325–327, 383.1,
222/541.3, 541.7–541.8
See application file for complete search history.

(56) References Cited

U.S. PATENT DOCUMENTS

| | | | |
|---|---|---|---|
| 5,846,058 A | 12/1998 | Fischer | |
| 5,860,739 A | 1/1999 | Cannon | |
| 6,095,813 A * | 8/2000 | Broyles | A61C 5/62 433/80 |
| 6,116,900 A * | 9/2000 | Ostler | A61C 5/00 433/89 |
| 6,352,177 B1 | 3/2002 | Bublewitz et al. | |
| 7,530,808 B2 | 5/2009 | Cao et al. | |
| 7,661,565 B2 * | 2/2010 | Jackman | B65D 51/20 215/232 |
| 7,861,893 B2 * | 1/2011 | Voegele | B05C 17/00553 222/137 |
| 7,922,486 B2 | 4/2011 | Pauser | |
| 8,262,890 B2 | 9/2012 | Meade | |
| 8,596,499 B2 | 12/2013 | Vogt et al. | |
| 8,747,113 B2 | 6/2014 | Brown et al. | |
| 8,875,947 B2 | 11/2014 | Obrist et al. | |
| 9,016,522 B2 * | 4/2015 | Hayman | B01F 5/0615 222/137 |
| 9,173,530 B2 * | 11/2015 | Fallat, II | A45D 34/04 |
| 9,707,052 B2 * | 7/2017 | Tapocik | A61C 19/066 |
| 2007/0108231 A1 * | 5/2007 | Gray | B01F 5/0603 222/135 |
| 2008/0311057 A1 * | 12/2008 | Larsen | A61C 19/066 424/51 |
| 2012/0258418 A1 * | 10/2012 | Shen | A61C 17/005 433/29 |
| 2012/0258424 A1 * | 10/2012 | Falsafi | A61K 6/0017 433/90 |
| 2014/0203042 A1 * | 7/2014 | Tsai | B65D 83/0033 222/80 |
| 2014/0252025 A1 * | 9/2014 | Schmid | B05C 17/0103 222/41 |
| 2014/0346190 A1 * | 11/2014 | Buck | B05C 17/0133 222/137 |
| 2018/0022526 A1 | 1/2018 | Demarest | |

OTHER PUBLICATIONS

LOCTITE, "Static mix nozzles for expoxy and other two part adhesives," LOCTITE, http://equipment.loctite.com/catDisplay.cfm?productLine=Two%20Part%20Dispensing&p1=23&categoryID=254&category=Static%20mix%20nozzles%20for%20epoxy%20and%20other%20two%20part%20adhesives, accessed Apr. 24, 2014, 1 page.

International Search Report and Written Opinion of the International Searching Authority in International Application No. PCT/US2015/045829, dated Mar. 9, 2016.

* cited by examiner

MULTI-CHEMISTRY DISPENSER

BACKGROUND

Whitening of teeth in a home environment is now a common and routine oral care activity. The whitening process can include the use of oral care strips that are placed into contact with the surface of the teeth, where the oral care strips include an embedded whitener. Whitening may also include the use of a chemically active whitening solution placed within a tray. The tray is positioned over the teeth such that the whitening solution is in physical contact with the teeth. The tray remains in place over the teeth for a period of time during the whitening process.

The whitener itself can be a bleach or another chemically active whitening gel or solution that chemically reacts with tooth discolorations. Some prior tooth whiteners have been packaged as a homogeneous mixture of active and inactive ingredients within a container such as a plastic bottle. An amount of solution is dispensed by the user from the bottle onto the tray.

New whiteners are being continually developed. A more convenient and/or efficacious tooth whitening package that dispenses a tooth whitening product would be desirable.

BRIEF SUMMARY

In an embodiment, a dispenser can include a plunger having a first arm, a second arm, and a channel that spaces the first arm from the second arm, wherein the plunger is disposed along a first axis, a housing that defines a first chamber, a second chamber, a wall that separates the first chamber from the second chamber, a first channel in fluid communication with the first chamber, a second channel in fluid communication with the second chamber, and a third channel. The first channel and the second channel may intersect to connect with the third channel. The third channel may be disposed along a second axis that intersects the first axis at an angle of from 10° to 170°, and the dispenser may further include a nozzle at an end of the third channel.

In another embodiment, a dispenser for a tooth whitening solution can include a housing defining a first chamber, a second chamber, and an applicator, a first liquid disposed within the first chamber and a second liquid disposed within the second chamber, and a plunger comprising a first arm positioned to move within the first chamber and a second arm positioned to move within the second chamber. The dispenser can further include a first channel defined by the applicator and positioned to receive the first liquid from the first chamber, a second channel defined by the applicator and positioned to receive the second liquid from the second chamber, wherein the first channel and the second channel are connected at an intersection, a third channel defined by the applicator, wherein the third channel is in fluid communication with the first channel and the second channel at the intersection, and a nozzle at an end of the applicator and at an end of the third channel.

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
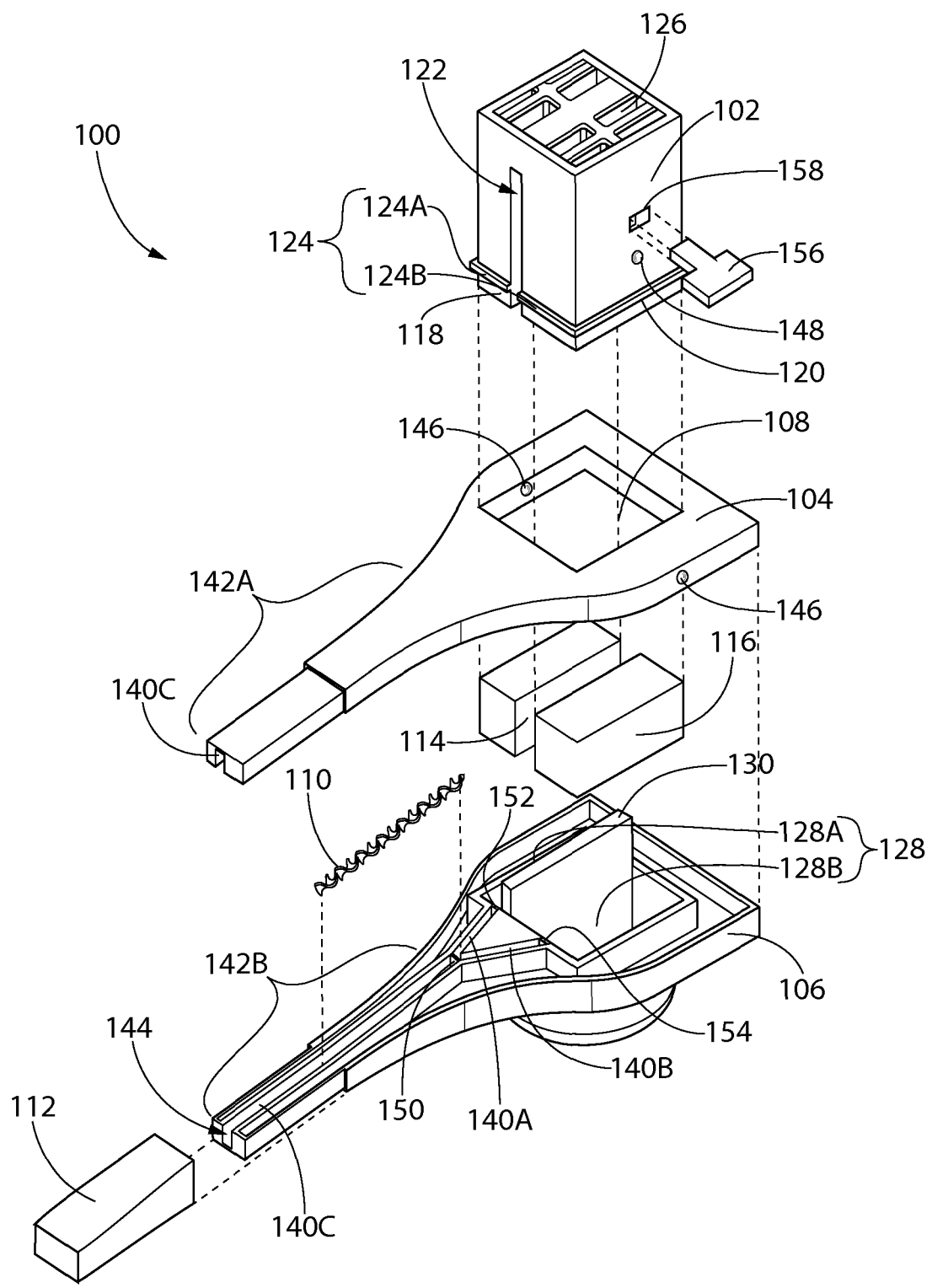
FIG. 1 is an exploded perspective depiction of a dispenser for a pair of gels or other liquids that are mixed together to form a single homogenous liquid such as a tooth whitening liquid.

It should be noted that some details of the FIGS. have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same or like parts. The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. As used herein, the terms "sufficiently mix" and "sufficiently mixed" may be used to describe an amount or degree of mixing of components such that the components physically contact each other and could, can, or will chemically react with each other. In various implementations where the components are reactive in a manner making them incompatible for storage before use in contact with each other, the components may be segregated from one another when not in use, i.e., prevented by the structure of the dispenser from sufficiently mixing when not in use. As used herein, the term "incompatible" may be used to describe components of a formulation that, when mixed and then stored for a length of time, degrade one or more desired qualities of the combined formulation.

As discussed above, prior tooth whitening solutions have been packaged as a homogeneous mixture of active and inactive ingredients within a container such as a plastic bottle. The volume of solution within the container is suitable for several uses or whitening treatments. An amount of such solution is dispensed from the bottle onto the tray by the user. However, the amount of solution dispensed is at the discretion of the user, and thus the dosage may not be well controlled. A user may easily dispense an excess or insufficient amount of solution into a tray.

Additionally, new types of whiteners are being continually developed. Some new whiteners may include two (or more) components (e.g., ingredients, compounds, mixtures, or formulations) that are required to be mixed together during use so as to have a whitening effect, but may not be stored compatibly in physical contact with each other. For example, over a relatively shorter duration of time, the two components can be mixed together and are suitable for use as a tooth whitener. However, over a relatively longer duration of time, the components may chemically interact after mixing and can become either more inert, and thus less effective as a tooth whitener, or more chemically active in a manner that is damaging or otherwise unsuitable for physical contact with teeth, gums, or other oral tissues. Other components, such as an aqueous component and a hydrophobic component, may physically separate quickly after mixing, for example, during shipping and storage and prior to use, and thus become ineffective or otherwise unsuitable as a tooth whitener.

An embodiment of the present teachings can include a dispenser for a tooth whitener. A user may use the dispenser to both mix the components of the whitener immediately prior to use and dispense the whitener into a tray or directly onto the teeth or another surface. The dispenser may be designed to dispense a controlled amount of whitener, thereby ensuring that the volume of whitener dispensed is neither insufficient nor excessive. While the present teachings are described with reference to the mixing of two chemical components, it will be understood that embodiments may also include a dispenser for a single homogeneous solution, or a dispenser for mixing more than two chemical components.

Figure 2:
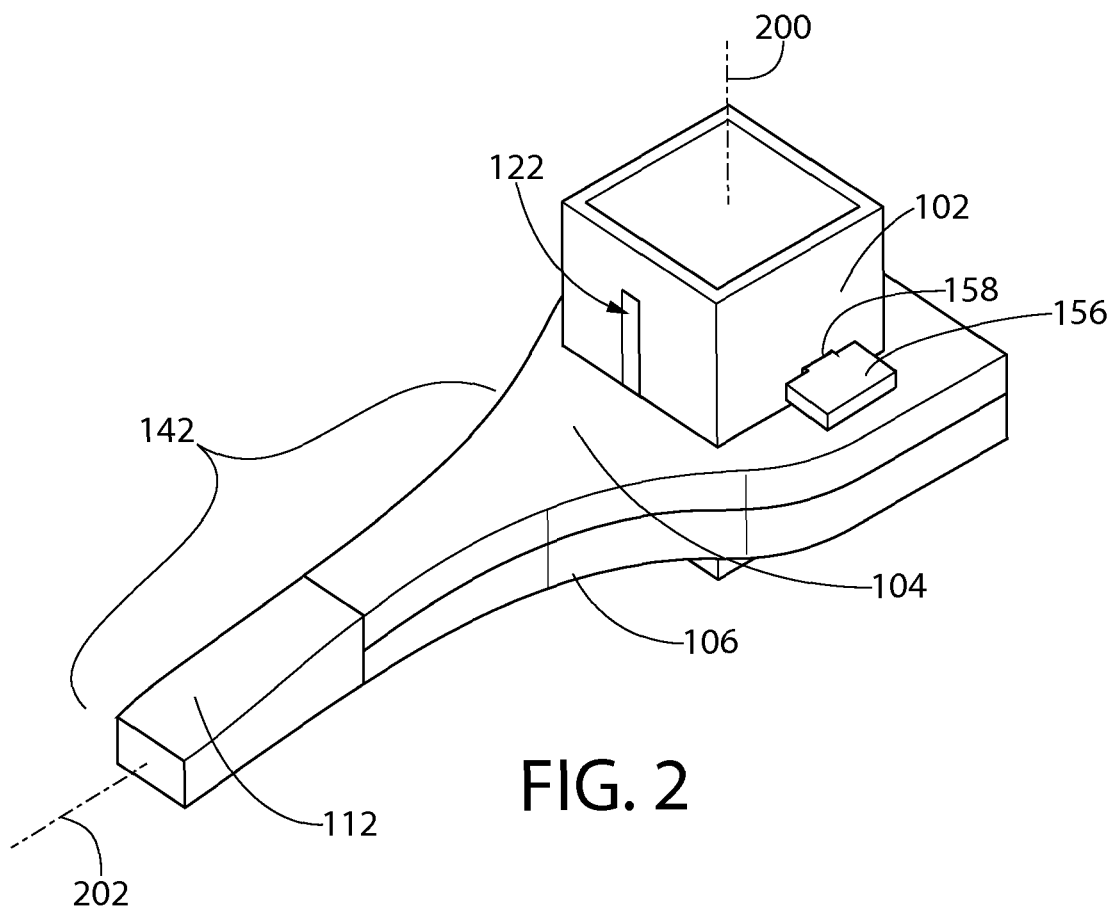
FIG. 2 is a perspective depiction of the FIG. 1 structure after assembly.

FIG. 1 is an exploded perspective view, and FIG. 2 is an assembled perspective view, of an embodiment for a tooth whitener dispenser 100. It will be understood that FIGS. 1 and 2 depict an exemplary assembly, and that a dispenser in accordance with an embodiment of the present teachings may include other structures that are not depicted for simplicity, while various depicted structures may be removed or modified. Other dispenser constructions are contemplated within the scope of this disclosure.

The embodiment of FIGS. 1 and 2 includes a piston or plunger 102, a first housing section 104, a second housing section 106, a static mixer 110, and an end cap 112. During use, the first housing section 104 and the second housing section 106 are attached together to provide a dispenser housing. FIG. 1 further depicts a first whitener component 114, such as a first gel, and a second whitener component 116, such as a second gel. In an embodiment, the first gel 114 and the second gel 116 are chemical components that are mixed together prior to use. Over a short duration of time, the gels 114, 116 may be compatibly mixed but, over a longer duration of time, they may not be compatibly mixed and are incompatible. For example, over a longer duration of time, the mixed gels 114, 116 may physically separate or chemically interact in an unfavorable manner such that the mixed gels become unsuitable for use as a tooth whitener.

In an embodiment, the plunger 102 may be a bifurcated plunger 102 including a first arm 118 and a second arm 120 separated by a channel 122 that spaces the first arm 118 from the second arm 120. Each arm 118, 120 may have a rounded "D"-shaped perimeter, or another shaped perimeter, depending on the design. The plunger 102 can further include a plunger seal 124. In an embodiment, the plunger seal 124 may include a first O-ring or other plunger seal 124A that encircles the first arm 118 and a second O-ring or other plunger seal 124B that encircles the second arm 120. Each O-ring may be positioned within a channel in one of the arms 118, 120 such that each O-ring conforms to the shape of each arm 118, 120. The O-rings 124A, 124B may be manufactured from a flexible material, for example, a rubber, a silicon, a polymer, or another suitable material. In another embodiment, the plunger seal 124 may be manufactured integral with the plunger 102 such that the plunger 102 and plunger seal 124 are a single piece of material, for example, if the plunger 102 is manufactured from a semi-rigid material that functions sufficiently as a plunger, but has some flexibility to provide a seal through physical contact with the one or both of the first housing section 104 and the second housing section 106. During use, the plunger seal 124 may prevent the gels 114, 116 from being forced between the walls of the plunger 102 and the walls of the first housing section 104 and/or the second housing section 106 during dispensing of the gels 114, 116, as described in more detail below.

To reduce the amount of material that forms the plunger 102, for example to decrease costs and weight, the plunger 102 may include an internal lattice structure 126 as depicted. Further, it is contemplated that the first housing section 104 and the second housing section 106 may be manufactured from a single piece of material using, for example, a molding process or an additive manufacturing process. The mixer 110 may be a separately manufactured, or manufactured as part of the housing.

The first housing section 104 may be manufactured to define a ring having an opening 108 therethrough. The second housing section 106 may be manufactured to define a pair of "D"-shaped chambers, including a first chamber 128A and a second chamber 128B, separated by a wall 130. The wall 130 is elongated to extend through, and fit within, the ring 130 of the first housing section 104. Prior to mixing, the first gel 114 is stored in the first chamber 128A and the second gel 116 is stored in the second chamber 128B. Prior to use, the gels 114, 116, which are whitener components, are stored separately and held in place within the chambers 128 closed in by the arms 118, 120, the first housing section 104 and the second housing section 106, including the wall 130.

The first housing section 104 and the second housing section 106, when assembled, can together define a first channel 140A, a second channel 140B, and a third channel 140C within an elongated applicator 142. The first channel 140A and the second channel 140B intersect at the third channel 140C, which is continuous with the first channel 140A and the second channel 140B. The third channel 140C may end or terminate in a nozzle 144 from which whitener is dispensed during use of the dispenser 100. Each of the channels 140A-140C may be formed in one or both of the first housing section 104 and/or the second housing section 106. When positioned on the end of the elongated applicator 142, the end cap 112 covers the end of the elongated applicator 142 and the nozzle 144, and prevents contamination of the end of the elongated applicator 142 and the nozzle 144.

In the depicted embodiment, the static mixer 110 may be a helix-type static mixer that is positioned within the third channel 140C. Other types of static mixers may be used. In some embodiments, the static mixer 110 may include one or more plates or baffles. The static mixer 110 may be integral with the walls of the third channel 140C, such that the static mixing structures is formed integral with one or both of the first housing section and/or the second housing section. In an embodiment, the static mixer 110 and one of the housing sections 104, 106 may be formed from one single continuous piece of material.

To prevent the first gel 114 and the second gel 116 from prematurely mixing within one or more of the channels 140A-140C, the dispenser 100 may include one or more frangible seals. In an embodiment, a frangible seal 150 may be formed within the third channel 140C at the intersection of the first channel 140A and the second channel 140B as depicted in FIG. 1. In this embodiment, the first gel 114 may enter the first channel 140A and the second gel 116 may enter the second channel 140B during storage of the dispenser 100, but the frangible seal 150 at the intersection of the first channel 140A and the second channel 140B prevents mixing of gels 114, 116. In another embodiment, a first frangible seal 152 may be formed to block the first channel 140A, and a second frangible seal 154 may be formed to block the second channel 140B, to prevent the first gel 114 and the second gel 116 from entering the third channel 140C and prematurely mixing. In another embodiment, all three frangible seals 150-154 may be used to prevent premature mixing of the gels 114, 116. The frangible seals 150-154 may be manufactured from a thin, flexible sheet, such as a rubber sheet, a silicone sheet, a foil sheet, a polymer sheet, or another suitable material. During storage, the one or more frangible seals 150-154 are unbroken and positioned to prevent the gels 114, 116 from entering one or more of the channels 140A-140C.

To prevent accidental actuation of the plunger 102, the dispenser may include a locking mechanism. While FIGS. 1 and 2 depict a locking mechanism in the form of a removable tab 156 that is pressure fit within a slot 158 in the plunger 102, other locking mechanisms are contemplated. In the embodiment depicted, the removable tab 156 extends from a side of the plunger 102 and physically contacts a surface of the first housing section 104 when in the locked position as depicted in FIG. 2. The removable tab 156 prevents inadvertent actuation of the plunger 102 prior to intentional dispensing of the whitener.

During use of the dispenser 100, a user may grasp the dispenser 100 with, for example, a thumb on a top surface of the plunger 102 and an index finger on a bottom surface of the second housing section 106. The user removes the end cap 112 from the elongated applicator 142, for example by sliding it from the elongated applicator 142, and unlocks the locking mechanism, for example, by sliding the removable tab 156 from the slot 158 in the plunger 102. The user then begins to pinch the dispenser 100, which places pressure on the plunger 102 and depresses the plunger 102, and forces the plunger 102 to slide or move within the chambers 128A, 128B. The pressure placed on the plunger 102 is transferred to the gels 114, 116 and forces the gels 114, 116 to rupture the one or more frangible seals 150-154. The one or more frangible seals 150-154 may be sized and configured to rupture at a pressure that is sufficiently low that, during the application of pressure on the plunger 102, the plunger seals 124A, 124B around the arms 118, 120 of the plunger 102 prevent the gels 114, 116 from being forced between the side of the plunger 102 and the inside edge of the chambers 128A, 128B, and out of the dispenser 100 through, for example, the opening 108 within the first housing section 104.

After rupturing the one or more frangible seals 150-154, the first channel 140A is in fluid communication with the first chamber 128A, and the second channel 140B is in fluid communication with the second chamber 128B. The third channel 140C, being connected at the intersection of the first channel 140A and the second channel 140B, is in fluid communication with the first channel 140A and the second channel 140B, and is thus also in fluid communication with the first chamber 128A and the second chamber 128B.

During continued pressure as the plunger 102 continues to slide or move within the chambers 128, the first gel 114 is forced to exit the first chamber 128A and enter the first channel 140A, and the second gel 116 is forced to exit the second chamber 128B and enter the second channel 140B. With continued pressure on, and sliding of, the plunger 102, the first gel 114 and the second gel 116 then enter the third channel 140C.

Figure 3:
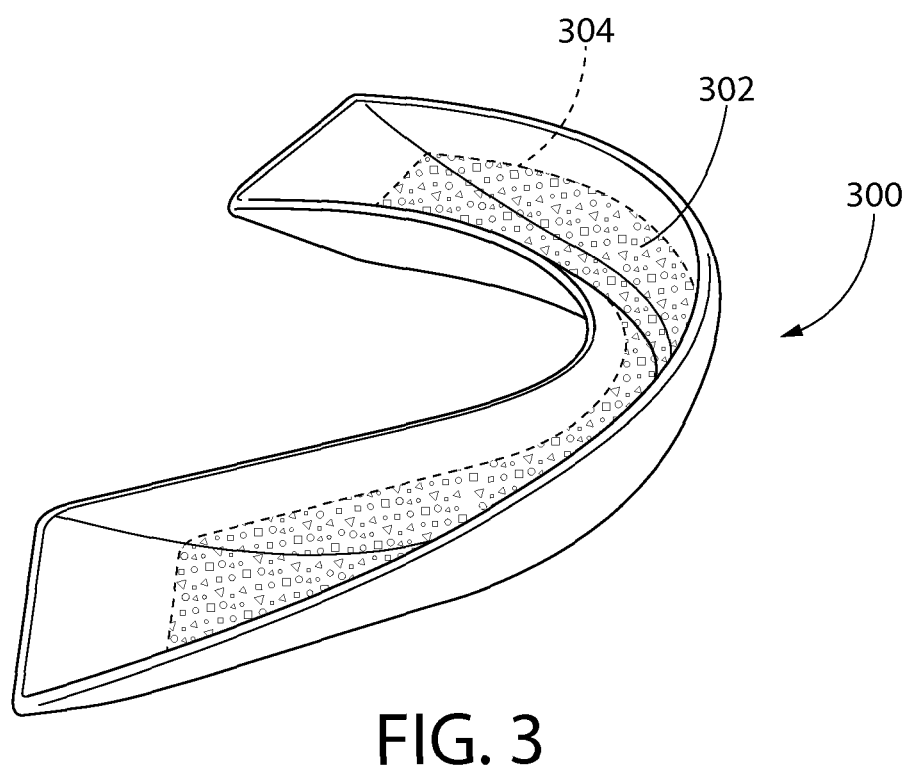
FIG. 3 is a perspective depiction of a tray having a homogenous liquid dispensed within a recess in the tray.

Upon entering the third channel 140C, the first gel 114 and the second gel 116 may physically contact each other and may begin to mix. Continued pressure on, and sliding of, the plunger 102 then forces the gels 114, 116 to travel through the static mixer 110 within the third channel 140C. After passing completely through the static mixer 110, the gels 114, 116 may be sufficiently mixed just prior to use. Upon mixing, the first gel 114 and the second gel 116 form, for example, a homogenous or substantially homogenous tooth whitening gel 304 (FIG. 3).

Continued pressure on, and sliding movement of, the plunger 102 forces the mixed tooth whitening gel 304 to exit the nozzle 144 at the end of the elongated applicator 142. The tooth whitening gel 304 may be dispensed from the nozzle 144 directly onto the user's teeth, into a recess 302 within a tray 300 as depicted in the perspective depiction of FIG. 3, or onto another intermediate surface, e.g., an applicator appliance, before physically contacting the teeth of the user. The tray 300, if used, is then placed over the user's teeth, with the teeth in the cavity 302, where the tooth whitening gel 304 physically contacts and whitens the user's teeth.

As depicted in FIGS. 1 and 2, the first arm 118 of the plunger 102 is configured to move through the first chamber 128A, and the second arm 120 of the plunger 102 is configured to move through the second chamber 128B, in a generally first direction (e.g., vertically with respect to the orientation of FIGS. 1 and 2) during dispensing of the gels 114, 116. As is further depicted, the gels 114, 116 travel through the channels 140A-140C of the elongated applicator 142 and exit the nozzle 144 in a generally second direction (e.g., horizontally with respect to the orientation of FIGS. 1 and 2) during dispensing of the mixed gels 114, 116. In other words, the plunger 102 is disposed along, and configured to move along, a first axis 200 (FIG. 2), while the third channel 140C is disposed along a second axis 202, wherein the second axis 202 intersects the first axis 200. In an embodiment, the second axis 202 may intersect the first axis 200 at an angle of from about 10° to about 170, or from about 30° to about 120°, or from about 60° to about 120°, for example about 90°. In another embodiment, the second axis may intersect the first axis at an angle of from about 30° to about 90°, or from about 60° to about 90°. In an embodiment, the elongated applicator 142 may be straight or curved.

It is contemplated that the plunger 102, first housing section 104, second housing section 106, and end cap 112 may be manufactured from plastic, another polymer, or another suitable material. The plunger 102, first housing section 104, second housing section 106, and end cap 112 may be manufactured from an opaque material, a translucent material, or a transparent material.

In an embodiment, a dispenser 100 may store a sufficient amount of gel 114, 116 to whiten only a user's upper teeth or only a user's lower teeth. In this embodiment, if the user desires to whiten both the upper teeth and the lower teeth, the entire contents of a first dispenser 100, less any waste that remains within the first dispenser, are placed into a first tray 300 and used to whiten the upper teeth. The contents of a second dispenser, less any waste that remains within the second dispenser, are placed into a second tray 300 and used to whiten the lower teeth.

In another embodiment, a dispenser 100 may store a sufficient amount of gel 114, 116 to whiten both a user's upper teeth and lower teeth. In this embodiment, a first half of the contents of a dispenser 100 may be dispensed into a first tray 300 and a second half of the contents of the dispenser 100 may be dispensed into a second tray 300. This embodiment may optionally include an indicator that indicates when half or approximately half of the gels 114, 116 have been dispensed. The indicator may provide a visual or tactile indication once the first half of the contents is dispensed. In an embodiment, one or more transparent windows 146 in the first housing section 104 may align with one or more indicator marks 148 on the plunger 102 once the first half of the contents have been discharged from the dispenser 100 as depicted in FIG. 1. In this embodiment, the one or more indicator marks 148 are seen through the one or more windows 146 to provide a visual indication that the first half of the dispenser contents have been dispensed from the dispenser. In another embodiment (not individually depicted for simplicity), one or more recesses in the first housing section align with one or more bumps or other protrusions in the plunger 102 once the first half of the contents has been dispensed from the dispenser. In this embodiment, the one or more bumps enter the one or more recesses once the first half of the dispenser contents have been dispensed from the dispenser to provide a tactile indicator through the use of a detent mechanism that the first half of the dispenser contents have been dispensed from the dispenser. In another embodiment (not individually depicted for simplicity) a line or other mark on the plunger 102 may align with a reference point such as an opening rim around one or both chambers 128 in the first housing section 104. In another embodiment (not individually depicted for simplicity), a bump on either the first housing section 104 or the second housing section 106 aligns with and enters the slot 158 that is part of the locking mechanism once half the whitener has been dispensed. In this embodiment, the slot 158 functions as both a part of the locking mechanism and as a part of a detent mechanism that indicates when half the whitener has been dispensed. Upon further pressure, the detent mechanism releases to allow dispensing of the remainder of the tooth whitener (less any waste).

It will be appreciated that, in the FIG. 1 embodiment, the first arm 118, the first chamber 128A and the first channel 140A are the same size as the second arm 120, the second chamber 128B, and the second channel 140B, respectively. In this embodiment, approximately equal parts of the first gel 114 and the second gel 116 are mixed to form the tooth whitener 304. In another embodiment, the structures may be sized differently so that unequal parts of the first gel 114 and the second gel 116 are mixed and dispensed to form the tooth whitener 304. For example, the first arm 118 may have a first volume or cross sectional area and the second arm may have a second volume or cross sectional area, where the second volume or cross sectional area is different than, for example, two times (or another multiplier of), the first volume or cross sectional area. Similarly, the first chamber 128A may have a first volume and the second chamber 128B may have a second volume, where the second volume is different than, for example, two times (or another multiplier of), the first volume. Additionally, the first channel 140A may have a first volume or cross sectional area and the second channel 140B may have a second volume or cross sectional area, where the second volume or cross sectional area is twice (or another multiplier of) the first volume or cross sectional area. In this embodiment, the tooth whiter may include an amount of the second gel 116 that is, for example, twice an amount of the first gel 114, or another amount depending on the formulation of the tooth whitener comprising the mixed first gel 114 and second gel 116.

While the embodiments described above have been discussed relative to two or more liquids in gel form that are mixed to form a homogenous tooth whitener, it will be appreciated that embodiments may apply to two or more other liquids of the same, different, or varying viscosities for uses other than a tooth whitener. Further, while the embodiments described above may include a separate static mixer to mix the gels, other mixers, including a tortuous path molded along with the first housing section and the second housing section, are contemplated.

In an embodiment, a home tooth whitening kit may include a plurality of dispensers 100. The number of dispensers may be equal to twice the number of whole-mouth treatments, where each dispenser includes a sufficient quantity of gel to treat either the upper teeth or the lower teeth, but not both. In another embodiment, the number of dispensers may equal the number of whole-mouth treatments, where each dispenser includes a sufficient quantity of gel to treat both the upper and lower teeth, where a first half of the gel in one dispenser is used to treat the upper teeth and the remaining second half of the gel is used to treat the lower teeth, or vice versa. In an embodiment, a home whitening kit may include two reusable trays, one for a user's upper teeth and one for a user's lower teeth. After a whitening treatment, the reusable trays are washed and reused for subsequent treatments. In another embodiment, a home whitening kit may include a number of disposable trays, where the number of disposable trays is equal to twice the number of whole-mouth treatments. After a whitening treatment, the disposable trays may be discarded or recycled.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "on" used with respect to two materials, one "on" the other, means at least some contact between the materials, while "over" and "overlie" mean the materials are in proximity, but possibly with one or more additional intervening materials such that physical contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present teachings will be apparent to those skilled in the art from consideration of the specification and practice of the disclosure herein. It is intended that the specification and examples be considered as exemplary only, with a true scope and spirit of the present teachings being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

What is claimed is:

1. A dispenser, comprising:
   a plunger comprising a first arm, a second arm, and a channel that spaces the first arm from the second arm, wherein the plunger oriented to extend along a first axis;
   a housing that defines a first chamber, a second chamber, a wall that separates the first chamber from the second chamber, a first channel in fluid communication with the first chamber, a second channel in fluid communication with the second chamber, and a third channel, wherein:
   the first channel and the second channel intersect to connect with the third channel; and
   the third channel is disposed along a second axis that intersects the first axis at an angle of from 10° to 170°;
   a nozzle at an end of the third channel; and
   a locking mechanism that prevents the plunger from being depressed prior to unlocking of the locking mechanism, wherein the locking mechanism comprises a slot within the plunger and a removable tab inserted into the slot, wherein the locking mechanism prevents the plunger from being depressed prior to removal of the removable tab from the slot.

2. The dispenser of claim 1, further comprising a first liquid in the first chamber and a second liquid in the second chamber.

3. The dispenser of claim 1, further comprising at least one frangible seal within at least one of the first channel, the second channel, and the third channel, wherein the at least one frangible seal prevents fluid communication between the first chamber and the third channel and between the second chamber and the third channel when the at least one frangible seal is intact.

4. The dispenser of claim 1, wherein the third channel comprises a static mixer.

5. The dispenser of claim 1, further comprising a first plunger seal around the first arm and a second plunger seal around the second arm, wherein the first plunger seal and the second plunger seal comprise a material selected from the group consisting of rubber, silicone, and a polymer.

6. The dispenser of claim 1, wherein the first chamber comprises a first volume and the second chamber comprises a second volume, wherein the first volume is less than the second volume.

7. The dispenser of claim 1, wherein the housing further comprises:
   a first housing section comprising a ring having an opening therethrough; and
   a second housing section attached to the first housing section, wherein the second housing section comprises the wall and the wall extends through the opening in the ring.

8. The dispenser of claim 7, further comprising an indicator on the first housing section, wherein the indicator is configured to indicate when approximately half of a volume of the first chamber has been occupied by the first arm after a movement of the first arm and approximately half of a volume of the second chamber has been occupied by the second arm after a movement of the second arm.

9. The dispenser of claim 1, wherein the housing further comprises an elongated applicator that defines the third channel.

10. The dispenser of claim 9, further comprising a removable end cap positioned over an end of the elongated applicator and over the nozzle.

11. The dispenser of claim 1, wherein the second axis intersects the first axis at an angle of about 90°.

12. A dispenser for a tooth whitening solution, comprising:
    a housing defining a first chamber, a second chamber, and an applicator;
    a first liquid disposed within the first chamber and a second liquid disposed within the second chamber;
    a plunger comprising a first arm positioned to move within the first chamber and a second arm positioned to move within the second chamber, wherein the plunger is disposed along a first axis;
    a first channel defined by the applicator and positioned to receive the first liquid from the first chamber;
    a second channel defined by the applicator and positioned to receive the second liquid from the second chamber, wherein the first channel and the second channel are connected at an intersection;
    a third channel defined by the applicator, wherein the third channel is in fluid communication with the first channel and the second channel at the intersection and the third channel is disposed along a second axis that intersects the first axis at an angle of between 10° and 170°;
    a nozzle at an end of the applicator and at an end of the third channel; and a locking mechanism comprising a slot within the plunger and a removable tab that is inserted into the slot, wherein the locking mechanism prevents the plunger from being depressed prior to removal of the removable tab from the slot.

13. The dispenser of claim 12, further comprising at least one seal within at least one of the first channel, the second channel, and the third channel that prevents fluid communication between the first chamber and the third channel and between the second chamber and the third channel when the at least one seal is intact.

14. The dispenser of claim 13, wherein the seal is positioned to rupture during movement of the first arm within the first chamber and during movement of the second arm within the second chamber.

15. The dispenser of claim 13, wherein the seal is positioned to rupture to establish fluid communication between the first chamber and the first channel and to further establish fluid communication between the second chamber and the second channel.

16. The dispenser of claim 12, further comprising an indicator on the plunger, wherein the indicator is positioned to indicate when approximately half of a volume of the first chamber has been occupied by the first arm after a movement of the first arm, and is further positioned to indicate when approximately half of a volume of the second chamber has been occupied by the second arm after a movement of the second arm.

17. The dispenser of claim 12, wherein the applicator further comprises a mixer positioned to mix the first liquid with the second liquid.

18. The dispenser of claim 12, further comprising:
a wall defined by the housing and positioned between the first chamber and the second chamber;
a channel defined by the first arm and the second arm, wherein the channel spaces the first arm from the second arm, wherein the wall is positioned within the channel defined by the first arm and the second arm;
a first plunger seal that encircles the first arm;
a second plunger seal that encircles the second arm; and
a locking mechanism comprising a slot within the plunger and a removable tab that is inserted into the slot, wherein the locking mechanism prevents the plunger from being depressed prior to removal of the removable tab from the slot.

* * * * *